United States Patent [19]

Johnson et al.

[11] 4,117,234
[45] Sep. 26, 1978

[54] INTERMEDIATE IN THE SYNTHESIS OF ESTRONE

[75] Inventors: William S. Johnson, Portola; Paul A. Bartlett, El Cerrito, both of Calif.

[73] Assignee: The Board of Trustees of the Leland Stanford Junior University, Stanford, Calif.

[21] Appl. No.: 726,351

[22] Filed: Sep. 24, 1976

Related U.S. Application Data

[63] Continuation-in-part of Ser. No. 281,406, Aug. 17, 1972, abandoned.

[51] Int. Cl.$^2$ .............................................. C07C 69/78
[52] U.S. Cl. .................................. 560/107; 542/400; 260/239.55 R; 260/397; 260/397.3; 260/397.4; 260/397.5; 260/488.8 R; 260/590 R; 260/590 C; 260/609 R; 260/611 A; 260/613 D; 260/348.52; 560/255; 568/807; 260/340.3
[58] Field of Search ............ 260/476 R, 618 R, 611 A, 260/613 D, 488 CD, 448.8 R; 560/255, 107

[56] References Cited

U.S. PATENT DOCUMENTS 3,598,845   8/1971   Johnson .......................... 260/611 A

*Primary Examiner*—Jane S. Myers
*Attorney, Agent, or Firm*—Townsend and Townsend

[57] ABSTRACT

Estrogenic steroids are synthesized by combining under conditions favoring the formation of a trans-olefin, a γ-arylpropanal with a 5,5,8,8-tetraalkoxy Wittig reagent. After hydrolysis of the gem-diethers, the resulting dioxo is internally condensed to form a cyclopentenone. The ketone is reduced to an oxy group and the resulting 2-(6'-arylhex-3'-enyl-1)cyclopent-2-en-1-ol or derivative thereof is cyclized to the Δ$^{13,17}$-estrene, preferably 17-alkyl-Δ$^{13,17}$-estrene with the A ring aromatized. After epoxidation, the 17-alkyl derivative is rearranged to form the 13-alkyl-1,3,5(10)-estratien-17-one. New compounds are provided as intermediates and final products.

3 Claims, No Drawings

INTERMEDIATE IN THE SYNTHESIS OF ESTRONE

CROSS-REFERENCE TO RELATED APPLICATION

This application is a continuation-in-part of application Ser. No. 281,406, filed Aug. 17, 1972 now abandoned.

BACKGROUND OF THE INVENTION

1. Field of the Invention

The ability to prepare estriol compounds from simple intermediates provides many advantages. First, it avoids the dependence on natural products, which are subject to fluctuations in availability and economics. Secondly, complete synthesis frequently provides greater flexibility for the introduction of functionalities at various sites in the molecule. Finally, complete synthesis frequently provides greater overall yields than can be obtained from naturally occurring molecules, which may require extensive modification.

2. Description of the Prior Art

Johnson, Accounts of Chemical Research, page 1, January 1968, describes nonenzymic biogenetic-like olefinic cyclizations using aliphatic compounds. Johnson, et al., J. Am. Chem. Soc. 93 4332 (1971) discloses cyclizations of aliphatic compounds to steroidal structures employing an alkinyl terminating group. See also Abrams, et al., Bio-organic Chemistry, 1, 243 (1971).

SUMMARY OF THE INVENTION

A method is provided for preparing estrogenic compounds from simple starting materials. A 3-aryl-propanal is condensed under conditions favoring trans-olefin formation with a 5,5,8,8-tetraalkoxy- or tetraalkylthio Wittig reagent. After hydrolysis of the gem-diethers, the dioxo is internally condensed to form a cyclopentenone. After reduction of the ketone to an oxy group, the resulting oxy compound is cyclized to form an A-aromatic $\Delta^{13,17}$-estrene, normally a 17-alkyl-$\Delta^{13,17}$-estrene. After epoxidation, and ring opening and where an alkyl group is present at C-17 rearrangement, an estrogenic steroid is obtained having an oxygen functionality at the 17 position. Intermediate compounds and transformation products thereof are provided.

DESCRIPTION OF THE SPECIFIC EMBODIMENTS

In accordance with this invention a γ-arylpropanal is condensed with an ω-$R^1$-5,5,8,5-tetralkoxyoctyl-1 Wittig reagent (triarylphosphonium salt) or tetraalkylthiom analog under conditions which favor the trans-olefin (Schlosser modification). The Wittig reagent is a triarylphosphonium halide salt which is combined with an aryl hydrocarbon lithium to form an ylid. The resulting olefin is hydrolyzed under mildly acidic conditions to form a dioxo compound, 1-aryl-8, 11-dioxo-12-$R^1$-dodec-3-ene, which is then condensed to form 2-(6'-arylhex-3'-en-1'-yl)-3-$R^1$-cyclopent-2-enone-1. After reduction of the ketone (oxo) to the 1-oxy, the alcohol is cyclized under strongly acidic conditions with a Lewis acid to 17-$R^1$-1,3,5(10),13(17)-estratetraene. The olefin is epoxidized, preferably through the formation of 13,17-halohydrin (particularly chloro- and bromohydrin) and base catalyzed epoxide formation. The $\Delta^{13,17}$-epoxide ring is opened under mildly acidic conditions, preferably employing an aprotic Lewis acid. With an alkyl substituent at C-17, the alkyl group migrates to the C-13, the α-epoxide giving the natural β-configuration.

For a further understanding of the invention, the following flow sheet is provided.

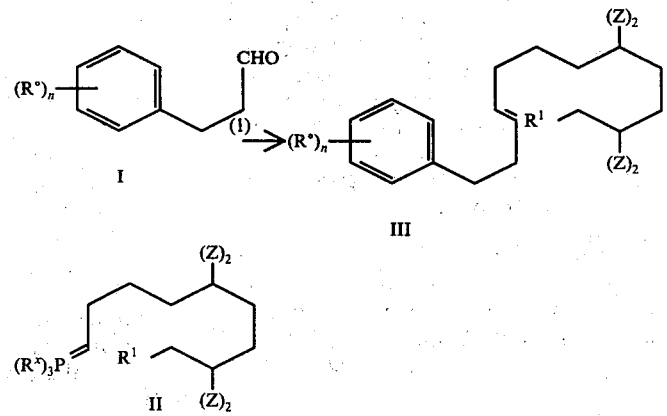

FLOW SHEET NO. I

FLOW SHEET NO. I
-continued

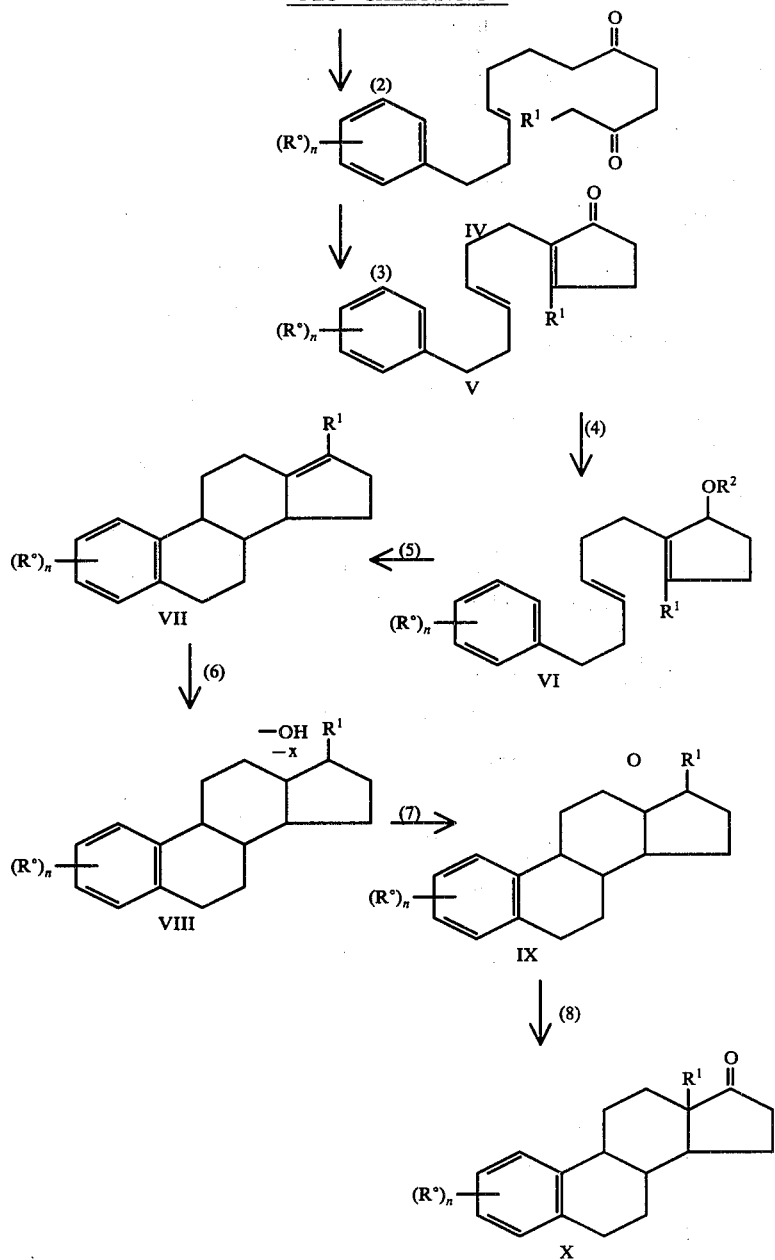

The symbols are defined as follows:

R° is alkyl from 1 to 4 carbon atoms, more usually from 1 to 2 carbon atoms, protected oxy, normally ethereal oxy (hydrocarbyloxy) of from 1 to 8 carbon atoms, normally having as its only aliphatic unsaturation from 0 to 1 site of ethylenic unsaturation or α-alkoxyalkoxy of from 2 to 6 carbon atoms, more usually from 2 to 4 carbon atoms, the groups being substituted so as to leave at least 1 ortho position vacant, preferred groups being oxy groups and preferably in the meta position;

n is from 0 to 2, generally 1;

Z is alkylchalcogenoxy, that is, alkoxy or alkylthio, each Z being of from 1 to 4 carbon atoms, preferably from 1 to 2 carbon atoms and preferably the two Z's are taken together to form a ring of from 5 to 6 members;

$R^x$ is arylhydrocarbon of from 6 to 10 carbon atoms, more usually from 6 to 7 carbon atoms;

$R^1$ is hydrogen or alkyl from 1 to 4 carbon atoms, preferably from 1 to 2 carbon atoms, and particularly preferred methyl; and $R^2$ is hydrogen, carboxyacyl of from 1 to 7 carbon atoms, tri(lower alkyl)silyl or lower alkyl, wherein lower alkyl is of from 1 to 4 carbon atoms.

(Hydrocarbyl is a monovalent radical of hydrogen and carbon, which may be aliphatically saturated or unsaturated, which may be aliphatic, alicyclic, aromatic or a combination thereof).

The intermediates are referred to by Roman numerals, but whenever an Arabic numeral appears of the same value, the Arabic numeral intends a particular species of the compound identified by a Roman numeral.

The various steps for the synthesis are indicated by Arabic numerals.

Some variation is permitted in the process, the significant aspect is the use of an aryl substituted aliphatic aldehyde which is condensed with a protected dioxo, usually diketone, to provide the desired dioxoolefin, which can then be used to form a cyclopentenone. After reduction and cyclization, further modification provides the desired product.

For purposes of illustration, in accordance with flow sheet No. 1, R° will initially be methoxy, substituted in the meta position, $n$ is 1, the two Z's are taken together to form an ethylenedioxy group, and $R^1$ is methyl.

Referring to the methoxy substituent, the ortho and para positions are activated and substitution could occur at any of these positions. However, due to steric reasons, only one of the ortho positions is likely to undergo internal cyclization, so that in fact there are only two possible products. The particular substituent bonded to the ring at the 3 position will affect the proportion ratio of substitution at the ortho and para positions.

Depending upon the position of attachment during cyclization, either of the following intermediates would be formed with R° in either the 1 or the 3 position.

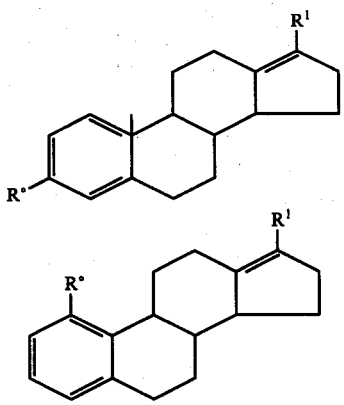

In carrying out the process of this invention, R° may be retained or may be modified at the various stages of the process. For some reactions, new protective groups are desirable. For example, in the preparation of estrone, the protective group for steps 1 and 2 is preferably methoxymethyl. During steps 3 and 4, no protective group is required, while during step 5, the preferred group is trimethylsilyl. This group has the advantage of providing substantial bulk, so as to sterically hinder cyclization at the ortho position. During step 6, carboxyacyl is a preferred group, which may be removed during step 7.

By using a trialkylsilyl group in the cyclization of step 5, enhanced yields of the 1 isomer can be obtained.

The protective group will, therefore, be primarily oxy groups, e.g., ethers and esters.

The ethereal protective group will generally be of from 1 to 8, usually 1 to 6 carbon atoms having from 0 to 1 oxygen atom which is preferably in the 2-position of the aliphatic chain bonded to the aryl oxygen. When there is 1 oxygen there will be at least 2 carbon atoms. The trialkyl silyl group will generally have from 3 to 9 carbon atoms, while the carboxyaryl will have from 1 to 8, usually 2 to 8 carbon atoms.

The epoxidation can be preformed in different ways and can lead to different results. One way is formation of the halohydrin (XIII), followed by elimination of hydrogen halide to form the epoxide. The epoxide is then alpha. Alternatively, one can prepare the epoxide directly employing a peracid, which provides the beta epoxide. Where an alkyl group is present at the 17 position, the alpha-epoxide provides the beta-alkyl at the 13 position, with the converse being true with the beta-epoxide.

The products are racemic, but any of the cyclic products may be resolved to obtain the natural stereoisomer.

PROCESS CONDITIONS

The general ranges of the conditions of the more important steps of the process will be indicated.

In step 1, the Schlosser modification of the Wittig reaction (see Schlosser, Angewandte Chemie, International Edition, 5 126 (1966)) the aldehyde and phosphonium salt are combined in approximately stoichiometric amounts, neither reagent being present in greater than 100 percent excess at a temperature below about −35° C, preferably from about −35° C to −100° C, followed by the addition of an approximately stoichiometric amount of arylhydrocarbon lithium, normally phenyllithium, at which time the reaction is warmed to a temperature of from about −50° to −15° C. Inert polar organic solvents are employed, particularly ethereal solvents, e.g., tetrahydrofuran. The reaction will be worked up in accordance with conventional techniques.

Internal condensation can be carried out in accordance with conventional base catalyzed diketone cyclizations. Conveniently, alkanolic hydroxide may be employed, for example, ethanolic sodium hydroxide. Generally, the concentration of hydroxide will range from about 0.01 to 0.1N.

The cyclization (step 5) employs a Lewis acid (either protic or aprotic). An inert aliphatic solvent, which may be protic or aprotic, is employed. Particularly useful solvents are inert halocarbons, both chloro and fluoro, normally of from 1 to 8 carbon atoms, and varying from monosubstituted to persubstituted, and having from 0 to 1 site of ethylenic unsaturation, the latter, particularly when polyhalo substituted. Haloethers may also be employed, normally of from 2 to 3 carbon atoms, the halogenated solvents being used by themselves or in combination with saturated hydrocarbons. Reactive monohalocarbons should be avoided.

The catalysts are strong Lewis acids. The protonic catalysts are strong acids, preferably carboxylic acids having a pK at 20° C in an aqueous solution of less than 4, preferably less than about 2. Illustrative strong protonic acids include trifluoroacetic acid, trichloroacetic acid, formic acid, etc. Illustrative aprotic Lewis acids include stannic chloride, titanium tetrachloride, zinc chloride, zinc bromide, boron trifluoride, etc. In the present invention, the aprotic Lewis acids are preferred.

The temperature of the reaction will generally be below 10° C, preferably below 0° C, and preferably in the range −10° to −110° C. Relatively dilute solutions will be employed, concentrations of the reactant being generally in the range of about 0.05 to 1M, more usually from about 0.1 to 0.5M. The amount of the catalyst will generally be from about 1 to 10 mole per mole of reactant, more usually for about 2 to 5 moles per mole of reactant.

The opening of the epoxide ring to the ketone is carried out in a conventional way employing an aprotic Lewis acid catalyst, preferably a mild Lewis acid catalyst such as etherated boron trifluoride, e.g., boron trifluoride diethyl ether. Moderate temperatures are employed, generally from about 0° to 40° C, preferably ambient. The reaction is carried out in an inert solvent for a short period of time, with a mole ratio of catalyst to epoxide in the range of about 1 to 3, more usually one to 1.5.

EXPERIMENTAL

In the following examples, where the phrase "usual workup" is used, it means that the organic layer was washed thoroughly with water and saturated in sodium chloride, dried over anhydrous sodium sulfate or potassium carbonate and the solvent removed under reduced pressure. Melting points were determined on a Kofler hot-stage microscope. Unless otherwise stated, nuclear magnetic resonance (nmr) spectra were determined on a Varian Associate T-60 NMR Spectrometer with deuteriochloroform solvent and tetramethylsilane as the internal reference. The chemical shifts are reported as $\delta$ values in ppm relative to tetramethylsilane equal to 0.

The symbol R refers to R° in flow sheet No. 1.

EXAMPLE 1

3-(m-Methoxyphenyl)propanal, 1 (R = CH$_3$O)

To a stirred suspension of 0.055 mole of methyl 3-(m-methoxyphenyl) propionate in 100 ml of dry tetrahydrofuran under nitrogen at −75° was added 0.073 mole of Red-Al in 25 ml of tetrahydrofuran over a 45 minute period. After 3 hours, the excess hydride was quenched by the slow addition of dry propionaldehyde and then by 20% H$_2$SO$_4$. The mixture was allowed to warm to room temperature, poured into water, and extracted with ether. The organic layer was washed with saturated NaHCO$_3$ and worked up in the usual way to give 9.5 g of crude product. This material was purified by evaporative bulb-to-bulb distillation (110°/0.01 mm) to give a 95% yield of aldehyde which contained no ester and less than 5% alcohol by glpc analysis.

| ir | $\lambda^{film}_{max}$ | 3.4 | | C—H |
|---|---|---|---|---|
| | | 3.56 | | CH$_3$—O |
| | | 3.68 | | aldehyde C—H |
| | | 5.80 | | C=O |
| | | 6.24, 6.33, 6.72, 6.90, 6.95, | | |
| | | | | phenyl nucleus |
| | | 8.7, 12.8, 14.4 | | |
| | | 7.95, 9.6 | | CH$_3$O—aromatic |
| nmr | $\delta$ 2.82 | A$_2$B$_2$m | 4H | —CH$_2$CH$_2$— |
| | 3.77 | s | 3H | CH$_3$O |
| | 6.6–7.3 | m | 4H | aromatic |
| | 9.78 | t(J=1Hz) | 1H | —CH=O |

EXAMPLE 2

Trans-1-(m-Methoxyphenyl)-8,11-bis(ethylenedioxy)-3-dodecene, 3 (R = CH$_3$O). Step 1

To a stirred suspension of 0.050 mole of 5,8-bis-(ethylenedioxy) nonyltriphenylphosphonium iodide in 170 ml of dry tetrahydrofuran under nitrogen was added 0.049 mole of phenyllithium in ether to generate the ylid 2. After 5 minutes the ylid solution was cooled to −75° and 0.045 mole (based on 95% purity) of 1 (R = CH$_3$O) in 38 ml of dry ether was added. After a 20 minute period at −70°; 0.052 mole of phenyllithium in ether was added to generate a second ylid intermediate and the solution was warmed to −30°. After 15 minutes, 5 ml of methanol was added and the reaction mixture was allowed to warm to room temperature. After 4.5 hours, the mixture was filtered into dilute NaHCO$_3$, extracted with ether, and the combined ether layer was washed with dilute Na$_2$S$_2$O$_3$, followed by the usual workup to give 24.5 g of crude product. This material was treated with 2.0 ml of phosphoryl chloride in 50 ml of pyridine to dehydrate the side product resulting from the reaction of the aldehyde with phenyllithium. After 10 minutes at room temperature, the mixture was poured into saturated NaHCO$_3$ and extracted with ether, followed by washing with saturated CuSO$_4$ and the usual workup to afford 19.8 g of yellow oil. After purification by chromatography on Florisil, 10.7 g (60% yield) of light yellow oil was obtained.

| calc'd for | C$_{23}$H$_{34}$O$_5$ | | C: 70.74%; H: 8.78% |
|---|---|---|---|
| found | | | C: 70.82%; H: 8.53% |
| ir | $\lambda^{film}_{max}$ | broad absorption | 8–10 ketals |
| | | 10.4 | trans olefin |
| nmr | $\delta$ 1.30 | s | 3H | —CH$_3$ (12) |
| | 1.53 | (t) | 2H | —CH$_2$— (7) |
| | 1.69 | s | 4H | —CH$_2$CH$_2$— (9,10) |
| | 1.3–2.8 | m | 8H | —CH$_2$— (1,2,5,6) |
| | 3.77 | s | 3H | CH$_3$O— |
| | 3.89 | s | 8H | —OCH$_2$CH$_2$O— |
| | 5.43 | (t) | 2H | olefinic |
| | 6.6–7.3 | m | 4H | aromatic |

To produce the ketal III or 3 with the olefinic group in the trans configuration, which is necessary for cyclization in Step 5, the Schlosser modification of the Wittig reaction was used. See Schlosser, Angewandte Chemie, International Edition, 5, p. 126 (1966).

EXAMPLE 3

3-Methyl-2-[trans-6-(m-methoxyphenyl)-3-hexenyl]-2-cyclopentenone, 5 (R = CH$_3$O). Steps 2 and 3

A solution of 0.013 mole of the diketal Wittig product 3 (R = CH$_3$O) in 250 ml of 95% ethanol and 125 ml of 0.1N HCl was degassed and heated under nitrogen at 50° for 5 hours. Then 250 ml of 0.1N NaOH was added, the solution was degassed, refluxed for 7 hours under nitrogen, and poured into 1:1 brine-water and the suspension was extracted with ether. The combined ether layer was worked up in the usual way to afford 3.58 g of crude product which was purified by evaporative distillation (180°/0.02 mm) to give 3.35 g (91% yield) of pale yellow liquid. An analytical sample was prepared in the same way.

| calc'd for | C$_{19}$H$_{24}$O$_2$ | | C: 80.26%; H: 8.51% |
|---|---|---|---|
| found | | | C: 80.11%; H: 8.44% |
| ir | $\lambda^{film}_{max}$ | 5.90, 6.07 | C=C—C=O |
| | | 10.4 | trans olefin |
| nmr $\delta$ 1.9–2.8 with peaks at 2.17 and 2.38 | | | |
| | | m | 12H | methylene |
| | 2.01 | s | 3H | 3-methyl |
| | 3.68 | s | 3H | CH$_3$O |
| | 5.45 | (t) | 2H | olefinic |
| | 6.6–7.4 | m | 4H | aromatic |

EXAMPLE 4

3-Methyl-2-[trans-6-(m-methoxyphenyl)-3-hexenyl]-2-cyclopentenol, 6 (R = CH$_3$O). Step 4

To a solution of 0.012 mole of the methoxy cyclopentenone 5 (R = CH$_3$O) in 50 ml of ether at 0° was added 0.012 mole of Red-Al in 5 ml of tetrahydrofuran. After 30 minutes, 0.1 ml of 0.1N NaOH was added and the suspension was worked up in the usual way to give 3.33 g (99% yield) of colorless oil which was carried through Step 5 immediately. An analytical sample was prepared by evaporative distillation (170°/0.05 mm).

| cal'd for | $C_{19}H_{26}O_2$ | | C: 79.68%; H: 9.15% |
|---|---|---|---|
| found | | | C: 79.86%; H: 9.06% |
| ir | $\lambda^{Film}_{max}$ | | 2.95 broad O—H |
| | | | 10.4 trans olefin |
| nmr δ 1.3–2.8 with a peak at 2.15 | | | |
| | | m | 13H methylene & methine |
| 1.65 | | s | 3H 3-methyl |
| 3.76 | | s | 3H $CH_3O$— |
| 4.7 | | broad | 1H —OH |
| 5.47 | | (t) | 2H olefinic |
| 6.7–7.4 | | m | 4H aromatic |

EXAMPLE 5

3-Methoxy- and 1-Methoxy-17-methyl-1,3,5(10), 13(17)-gonatetraene, 7a and 7b (R = $CH_3O$). Step 5

A solution of 0.030 mole of stannic chloride in 30 ml of dry methylene chloride was stirred under nitrogen at −100°. A solution of 0.010 mole of 6 (R = $CH_3O$) in 10 ml of methylene chloride was added slowly down the side of the flask. The yellow-orange solution was then frozen at −105° for 40 minutes, warmed to liquidity (−95°), and quenched with pyridine. The suspension was diluted with ether, filtered, washed with 1N HCl and then worked up in the usual way to give 2.39 g (86% recovery) of crude product. The isomers were separated by chromatography on silica gel to give 1.40 g (59% yield) of the 3-methoxy isomer 7a (R = $CH_3O$), mp 62°–77°, and 0.32 g (11% yield) of the 1-methoxy isomer 7b (R = $CH_3O$), mp 109°–111°. On a smaller scale (217 mg of 6 (R = $CH_3O$)) under similar conditions, yields of 59% and 12% for 7a and 7b (R = $CH_3O$), respectively, were obtained. An analytical sample of each was prepared by recrystallization from 95% ethanol.

Analytical data for 7b are as follows:

| cal'd for | $C_{19}H_{24}O$ | | C: 85.03%; H: 9.01% |
|---|---|---|---|
| found | | | C: 85.03%; H: 9.20% |
| ir | $\lambda^{CHCl_3}_{max}$ | | 3.40, 3.48 C—H |
| | 6.24(w), 6.32, 6.85, 6.95 (w) | | aromatic nucleus |
| | 8.0, 9.3 | | aromatic —$OCH_3$ |
| nmr | δ 0.8–3.2 | m | 15H methylene & methine |
| | 1.63 | s | 3H C-17 methyl |
| 3.76 | | s | 3H $CH_3O$— |
| 6.6 | | d(J=8Hz) | 2H H-2 & H-4 |
| 7.1 | | t(J=8Hz) | 1H H-3 |
| uv | MeOH max | | 272(log 3.34), 279(3.33) |

Analytical data for 7a are as follows: 3-methoxy-17-methyl-1,3,5(10), 13(17)-gonatetraene, (R = $CH_3O$), colorless, microcrystalline, mp 80.5°–81°

| calc'd for | $C_{19}H_{24}O$ | | C: 85.03%; H: 9.01% |
|---|---|---|---|
| found | | | C: 85.08%; H: 8.92% |
| ir | $\lambda^{CHCl_3}_{max}$ | | 3.40, 3.50 C—H |
| | 6.20, 6.36(w), 6.68, 6.9 | | aromatic nucleus |
| | 8.0, 9.7 | | aromatic —$OCH_3$ |
| | (lit.$^{19A}\lambda^{CHCl_3}_{max}$ 6.21, 6.34) | | |
| nmr | δ 0.8–3.0 | m | 15H methylene & methine |
| | 1.63 | s | 3H C-17 methyl |
| | 3.74 | s | 3H $CH_3O$— |
| | 6.70 | (t) | 1H H—4 |
| | 6.78 | dd | 1H H—2, $J_{1,2}$=8Hz, $J_{2,4}$=2Hz |
| | 7.23 | d | 1H H—1, $J_{1,2}$=8Hz |
| uv | $\lambda^{MeOH}_{max}$ 277(3.43), 286(3.39) | | (lit.$^{19B}\lambda^{MeOH}$ 277(3.35), 286(3.31)) |

EXAMPLE 6

3-Methoxy-17-methyl-13,17-epoxy-1,3,5 (10)-gonatriene, 9a (R = $CH_3O$). Steps 6 and 7

A solution of 0.43 mole of the methoxy tetracyclic olefin 7a (R = $CH_3O$) in 2.1 ml of 1:9 water-dimethoxyethene was treated with 0.45 mmole of N,N-dichloro-p-toluenesulfonamide at 0°. After 10 minutes, powdered sodium thiosulfate, ether and water were added and the suspension was stirred vigorously for 5 minutes. The flask was kept at 0° while the aqueous layer was removed by pipet and the ether layer was washed with water and concentrated to about 2 ml at reduced pressure. This solution of the crude chlorohydrin 8a was diluted with methanol and stirred with NaOH at room temperature for 45 minutes. The mixture was poured into water and the product was extracted with ether. After washing the ether layer with 1N NaOH to remove p-toluenesulfonamide, the usual workup afforded about 130 mg (theoretical:121 mg) of crude product. Purification by preparative thin layer chromatography afforded 34 mg (28% yield) of the epoxide, mp 130°–140°, which was shown to be essentially pure by glpc analysis; an analytical sample was purified by recrystallization from methanol, colorless needles, mp 151°–152°.

| calc'd for | $C_{19}H_{24}O_2$ | C: 80.24%; H: 8.51% |
|---|---|---|
| found | | C: 80.24%; H: 8.61% |

The ir spectrum showed no significant differences from that of the methoxy tetracyclic olefin 7a (R = $CH_3O$).

| nmr | δ 0.8–3.2 | m | 15H | methylene & methine |
|---|---|---|---|---|
| | 1.33 | s | 3H | C-17 methyl |
| | 3.73 | s | 3H | $CH_3O$— |
| | 6.70 | (t) | 1H | H-4 |
| | 6.78 | dd | 1H | H-2, $J_{1,2}$ = 8Hz, $J_{2,4}$ = 2Hz |
| | 7.23 | d | 1H | H-1, $J_{1,2}$ = 8Hz |

EXAMPLE 7

Estrone methylether, 10a (R = $CH_3O$). Step 8

A solution of 0.012 mmole of the methoxy epoxide 9a (R = $CH_3O$) in 1.51 ml of dry benzene was treated with 0.15 ml of boron trifluoride etherate for 1 minute at room temperature. The dark purple solution was diluted with ether and poured into rapidly stirred saturated $NaHCO_3$. After 5 minutes, the phases were separated and the usual workup afforded a quantitative yield of semi-crystalline material, mp about 80°–135°. After preparative thin layer chromatography, 21 mg (62% yield) of estrone methyl ether, mp 125°–135° was obtained. This material was further purified by sublimation and recrystallization from methanol, colorless prisms, mp 142°–144°, and shown to be identical to an authentic sample 143°–144°) by glpc coinjection, mixture melting point (142°–144°) and ir.

EXAMPLE 8

Methyl 3-(m-Methoxymethoxyphenyl)propionate

A suspension of 0.14 mole of methyl m-mydroxycinnamate and about 0.2 g of Adam's catalyst in 100 ml of methanol was stirred under hydrogen until hydrogen uptake ceased, and then filtered and the solvent was removed at reduced pressure. This crude methyl 3-(m-hydroxy-phenylpropionate) in 200 ml of tetrahydrofuran was added at 0° to 0.17 mole of sodium hydride. The mixture was stirred for 10 minutes, 0.19 mole of chloromethyl methyl ether was added and the thick suspension was stirred at room temperature for 20 minutes. The mixture was concentrated at reduced pressure to 100 ml, poured into dilute NaHCO$_3$ and extracted with ether. The organic layer was washed twice with 1N NaOH, followed by the usual workup to give 29.2 g (90% yield from methyl m-hydroxycinnamate) of liquid product. An analytical sample was prepared by evaporative distillation (150°/0.05 mm).

| calc'd for | | C$_{10}$H$_{16}$O$_4$ | | C: 64.27%; H: 7.19% |
|---|---|---|---|---|
| found | | | | C: 64.43%; H: 7.47% |
| ir | $\lambda_{max}^{film}$ | 3.4 | | C—H |
| | | 5.74 | | C=O |
| | | 6.20,6.30,6.72,6.91,6.97, | | |
| | | 8.7, 12.7, 10.4 | | phenyl nucleus |
| | | 8.0, 9.3, 9.9 | | acetal |
| nmr | δ 2.78 | A$_2$B$_2$m | 4H | —CH$_2$CH$_2$— |
| | 3.47 | s | 3H |  |
| | 3.67 | s | 3H | —CO$_2$CH$_3$ |
| | 5.16 | s | 2H | —OCH$_2$O— |
| | 6.7–7.3 | m | 4H | aromatic |

EXAMPLE 9

3-(m-Methoxymethoxyphenyl)propanal, 1 (R = CH$_3$OCH$_2$O)

A sample of 0.13 mole of methyl 3-(m-methoxymethoxyphenyl) propionate was reduced to a mixture of the aldehyde 1 (R = CH$_3$OCH$_2$O) and the corresponding alcohol (5:1 molar ratio) in 98% yield by the method of Example 1. This mixture was purified as follows: the crude aldehyde was washed with 5 ml of petane to remove a small amount of immiscible oil and then triturated with 300 ml of pentane. Upon concentration of this pentane layer, 9.2 g (38% yield) of aldehyde containing about 5% of the alcohol was obtained. The residue from the trituration (containing about 22% alcohol) in 50 ml of methylene chloride was oxidized by addition to a solution of Collins reagent prepared from 450 ml of methylene chloride, 0.165 mole of pyridine, 1 g of barium oxide, and 0.151 mole of chromium trioxide. After 15 minutes the dark mixture was filtered through 100 g of Florisil, followed by more methylene chloride, and the solvent was removed at reduced pressure to give 11.7 g (86% recovery) of light yellow aldehyde which was free of alcohol. Combined with the 95% pure fraction from the pentane-trituration, this yield represents an overall conversion of 84%.*

*Sample for analysis prepared by chromatography and evaporative distillation. Low values for combustion analysis probably due to oxidation of carboxylic acid.

| calc'd for | | C$_{11}$H$_{14}$O$_3$ | | C: 68.02%; H: 7.27% |
|---|---|---|---|---|
| found | | | | C: 67.14%; H: 7.07% |
| ir | $\lambda_{max}^{film}$ | 3.51,3.64 | | aldehyde C—H |
| | | 5.79 | | C=O |
| nmr | δ 2.82 | A$_2$B$_2$m | 4H | —CH$_2$CH$_2$— |
| | 3.46 | s | 3H | CH$_3$O— |
| | 5.13 | s | 2H | —OCH$_2$O— |
| | 6.6–7.3 | m | 4H | aromatic |
| | 9.78 | (t) | 1H | —CHO |

EXAMPLE 10

Trans-1-(m-methoxymethoxyphenyl)-8,11-bis(ethylenedioxy)-3-dodecene, 3 (R = CH$_3$OCH$_2$O). Step 1

1 from Example 10 was coupled with 5,8-bis(ethylenedioxy)nonyltriphenylphosphonium iodide by the method of Example 2 to afford the product 3 (R = CH$_3$OCH$_2$O) in 62% yield. An analytical sample was prepared by evaporative distillation (200°/0.025 mm).

| calc'd for | | C$_{24}$H$_{36}$O$_6$ | | C: 68.54%; H: 8.63% |
|---|---|---|---|---|
| found | | | | C: 68.82%; H: 8.62% |
| ir | $\lambda_{max}^{film}$ | broad absorption | | 8–10 ketals |
| | | 10.4 (shoulder) | | trans olefin |
| nmr (CCl$_4$) | δ 1.2–2.7 | m | 8 | —CH$_2$— (1,2,5,6) |
| | 1.40 | (t) | 2 | —CH$_2$—(7) |
| | 1.55 | s | 4 | —CH$_2$CH$_2$— (9,10) |
| | 1.21 | s | 3 | —CH$_3$ (12) |
| | 3.46 | s | 3 | CH$_3$O— |
| | 3.84 | s | 8 | —OCH$_2$CH$_2$O— |
| | 5.07 | s | 2 | —OCH$_2$O— |
| | 5.40 | (t) | 2 | olefinic |
| | 6.6–7.2 | m | 4 | aromatic |

Example 11

Trans-1-(m-hydroxyphenyl)-dodec-3-en-8,11 dione 4 (R = HO). Step 2

A solution of 4.8 mmoles of the bisketal methoxymethylether 3 (R = CH$_3$OCH$_2$O) in 40 ml of 3:1 methanol-water and 2 ml of 20% H$_2$SO$_4$ was refluxed for 1 hour and poured into saturated NaHCO$_3$. After extraction with ether and the usual work up, 0.95 g (100%) of light yellow oil was obtained. An analytical sample was prepared by evaporative distillation (200°/0.05 mm).

| calc'd for | | C$_{18}$H$_{24}$O$_3$ | | C: 74.97%; H: 8.39% |
|---|---|---|---|---|
| found | | | | C: 74.69%; H: 8.34% |
| ir | $\lambda_{max}^{film}$ | 2.9 | | O—H |
| | | 3.38 | | C—H |
| | | 5.84 | | C=O |
| | | 6.29,6.74(m),6.89 | | aromatic nucleus |
| | | 14.4 | | |
| nmr | δ 1.3–2.7 | m | 10H | —CH$_2$—(1,2,5,6,7) |
| | 2.67 | s | 4H | —CH$_2$CH$_2$—(9,10) |
| | 2.17 | s | 3H | —CH$_3$(12) |
| | 5.17 | (t) | 2H | olefinic |
| | 6.5–7.4 | m | 5H | —OH & aromatic |

EXAMPLE 12

3-Methyl-2-[trans-6-(m-hydroxyphenyl)-3-hexenyl]-2-cyclopentenone, 5 (R = HO). Step 3

The crude phenolic dione 4 (R = HO), as prepared from 0.022 mole of the diketal methoxymethyl ether 3 (R = CH$_3$OCH$_2$O) was dissolved in 350 ml of 95% ethanol. After the addition of 300 ml of water and 50 ml of 1N NaOH, the mixture was degassed and refluxed under nitrogen for 5 hours. The solution was poured into 1:1 brine-saturated NH$_4$Cl and the product was extracted with ether, washed with saturated NaHCO$_3$, and worked up in the usual way, affording 5.6 g (97% recovery) of brown solid. After purification by evaporative distillation (220°/0.015 mm) and recrystallization from di-isopropyl ether, a 56% yield of pure trans product, mp 86°–90°, was obtained. An analytical sample was purified by recrystallization from di-isopropyl ether, colorless prisms, mp 88°–91°.

| calc'd | C$_{18}$H$_{22}$O$_2$ | C: 79.96%; H: 8.20% |
|---|---|---|
| found | | C: 79.82%; H: 8.23% |

-continued

| ir | $\lambda_{max}^{CHCl_3}$ | 2.72,3.0 | | O—H |
| | | 3.39 | | C—H |
| | | 5.92,6.09 | | C=C—C=O |
| nmr | δ 1.8–2.7 with peaks at 2.15 and 2.40 | | | |
| | 1.98 | m | 12H | —CH$_2$— |
| | 5.38 | s | 3H | —CH$_3$ |
| | 6.5–7.3 | (t) | 2H | olefinic |
| | | m | 5H | —OH & aromatic |

EXAMPLE 13

3-Benzoyloxy-17-methyl-1,3,5(10),13(17)-gonatetraene, 7a (R = C$_6$H$_5$CO$_2$). Steps 4 and 5

A solution of 10.75 mmoles of the phenolic cyclopentenone 5 (R = HO) in 50 ml of dry tetrahydrofuran was treated with about 16 mmoles of Red-Al. After 0.5 hours at room temperature, the solution was transferred into ether and dilute (NH$_4$)$_2$SO$_4$. After extraction and separation of the phases, the aqueous layer was neutralized with solid (NH$_4$)$_2$SO$_4$ and reextracted with ether. The combined ether layer was washed twice with dilute NaHCO$_3$ and brine, dried over K$_2$CO$_3$, and concentrated under reduced pressure. The crude cyclopentenol 6 (R = HO) was immediately silylated by treatment with 5.95 mmoles of bis(trimethylsilyl) trifluoroacetamide and 1.1 mmole of triethylamine in 25 ml of dry acetonitrile at 0°. After 15 minutes the volatile materials were removed reduced pressure and the product was dissolved in ether, washed twice each with dilute NaHCO$_3$ and brine, dried over K$_2$CO$_3$, and concentrated under reduced pressure to give 3.9 g (theoretical 3.7 g) of colorless oil which was carried through Step 5 immediately.

A solution of 32.6 mmoles of stannic chloride in 32 ml of dry methylene chloride was stirred at −95° (internal thermometer) and the crude trimethylsilyl cyclopentenol 6 (R = CH$_3$)$_3$SiO) in 14 ml of dry methylene chloride was added slowly to it. After 20 minutes at −95°, the dark burgundy-colored solution was warmed to −75° and 50 ml of ether was added slowly (temperature < −75°) followed by 5 ml of pyridine. The white suspension was warmed to room temperature, poured into ether and filtered. The colorless solution was washed with dilute NaHCO$_3$ and then with saturated copper sulfate to remove the pyridine, followed by the usual work up to give 3.47 g (99% recovery) of pale yellow solid. This crude cyclization product was about 90% pure para isomer 7a (R = (CH$_3$)$_3$SiO) by glpc analysis.

After an unsuccessful attempt to convert the trimethylsilyl ether directly to the benzoate 7a (R = C$_6$H$_5$CO$_2$) by heating with benzoyl chloride and lithium chloride in pyridine, the trimethylsilyl group was completely hydrolyzed by brief (about 1 minute) reflux in methanol. After removal of the methanol at reduced pressure, the benzoate-phenol mixture was treated with 2 ml of benzoyl chloride in 25 ml of pyridine for 10 minutes, followed by 2 ml of 85% lactic acid for 10 minutes to destroy excess reagent. The mixture was poured into water, extracted with ether, and the ether layer was thoroughly washed with dilute H$_2$SO$_4$ and saturated NaHCO$_3$, followed by the usual work up to afford 4.02 g (theoretical yield 3.84 g) of brown crystalline solide, mp 100°–120°. An analytical sample was obtained by recrystallization from methanol, colorless plates, mp 114°–116°.

| calc'd for | C$_{25}$H$_{26}$O$_2$ | | | C: 83.76%; H: 7.31% |
| found | | | | C: 83.49%; H: 7.28% |
| ir | $\lambda_{max}^{CHCl_3}$ | 3.4,3.5 | | O—H |
| | | 5.77 | | C=O |
| | | 6.23,6.71,6.90 | | aromatic nucleus |
| | | 7.95,8.3 | | aromatic ester |
| nmr | δ 0.9–3.1 with peak at 2.22 | | | |
| | | m | 15H | methylene & methine |
| | 1.63 | s | 3H | —CH$_3$ |
| | 6.9–8.4 | m | 8H | aromatic |

EXAMPLE 14

Chlorohydrin of 3-Benzoyloxy-17-methyl-1,3,5(10),13(17)-gonatetraene, 8a (R = C$_6$H$_5$CO$_2$, X = Cl). Step 6

A solution of 0.50 mmole of the crude tetracyclic benzoate 7a (R = C$_6$H$_5$CO$_2$) as prepared in Example 13 in 2.5 ml of 1:9 water-dimethoxyethane was stirred at 0° and 0.52 mmole of N,N-dichloro-p-toluenesulfonamide was added. After 10 minutes, powdered sodium thiosulfate, ether and water were added and the mixture was stirred vigorously at 0° for 5 minutes. The aqueous layer was removed by pipet and the ether layer was washed with 1N NaOH, saturated NH$_4$Cl, and brine, dried over Na$_2$SO$_4$ and concentrated to a light yellow oil under reduced pressure. After purification by preparative thin layer chromatography, 78 mg (40% yield overall from the phenolic cyclopentenone 5 (R = HO)) of crystalline chlorohydrin was obtained, mp 160°–180°. An analytical sample was obtained by recrystallization from acetone, colorless plates, mp 183°–189°, melts and resolidifies at 165°.

| calc'd for | C$_{25}$H$_{27}$OCl | | | C: 73.07%; H: 6.62% |
| found | | | | C: 73.18%; H: 6.57% |
| ir | $\lambda_{max}^{CHCl_3}$ | | | 2.72, 2.9   O—H |
| nmr | δ 1.0–3.1 | m | 16H | —OH,methylene & Methine |
| | 1.50 | s | 3H | —CH$_3$ |
| | 6.9–8.3 | m | 8H | aromatic |

EXAMPLE 15

3-Hydroxy-17β-methyl-13,17α-epoxy-1,3,5(10)-gonatriene, 9a (R = HO). Step 7

A suspension of 0.19 mmole of the crude chlorohydrin benzoate 8a (R = C$_6$H$_5$CO$_2$, X = Cl) in 2 ml of dimethoxyethane, 4 ml of methanol and 1 ml of water was stirred with 150 mg of NaOH. After 45 minutes at room temperature, the homogeneous solution was poured into dilute NH$_4$Cl, and the product was extracted with ether. After washing with saturated NaHCO$_3$ and the usual work up, 58 mg (theoretical yield 51 mg) of pale yellow oil smelling of methyl benzoate was obtained. An analytical sample, purified by recrystallization from methanol, colorless prisms, melted and resolidified at 185° and melted from 196°–202° with sublimation and darkening.

| calc'd for | C$_{18}$H$_{22}$O$_2$ | | | C: 79.96%; H: 8.20% |
| found | | | | C: 79.76%; H: 8.18% |
| ir | $\lambda_{max}^{KBr}$ | 3.0 | | O—H |
| | | 3.4, 3.5 | | C—H |
| | | 6.16, 6.31, | | |
| | | 6.67, 6.9 | | aromatic nucleus |
| nmr | δ 0.8–2.9 | m | 15H | methylene & methine |
| | 1.36 | s | 3H | CH$_2$ |
| | 5.52 | s | 1H | —OH |
| | 6.56 | (s) | 1H | H-4 |
| | 6.64 | dd | 1H | H-2,$J_{1,2}$=8Hz, $J_{2,4}$=2Hz |

| 7.17 | d | 1H | H-1,$J_{1,2}$=8Hz |

EXAMPLE 16

Estrone, 10a (R = HO

A solution of 0.19 mmole of the crude phenolic epoxide 9a (R = HO) in 1.5 ml of dry benzene was treated with 0.2 ml of borontrifluoride etherate for 1 minute at room temperature, diluted with ether, and poured into rapidly stirred saturated NaHCO$_3$. After 5 minutes, the phases were separated and the organic layer was worked up in the usual way to afford 47 mg (92% yield based on chlorohydrin 8a) (R = C$_6$H$_5$CO$_2$, X = Cl) of orange solid, mp 190°-240° with sublimation. A portion (42 mg) of this crude product was recrystallized from ethyl acetate (two crops), and the mother liquors were purified by ptlc preparative thin layer chromatography to give a total of 19.0 mg (41% from the chlorohydrin, 16% from the phenolic cyclopentenone 5 (R = HO)) of dl-estrone, mp 240°-248° (lit.$^3$253°-255°). Recrystallization from acetone afforded colorless plates melting at 251°-252°, undepressed on admixture with an authentic specimen. This material was shown to be identical with authentic dl-estrone by glpc coinjection and by ir.

EXAMPLE 17

3-Methyl-2-[trans-6-m-hydroxyphenyl)-3-hexenyl]-2-cyclopentenol dibenzoate VI $^0$ = m-C$_6$H$_5$CO$_2$, R$^2$ = C$_6$H$_5$CO)

A solution of 0.20 mmole of the phenolic cyclopentenol 6 (R = HO) as prepared in Example 13, in 1 ml of dry pyridine was stirred with 0.70 mmole of benzoyl chloride for 0.5 hour at room temperature. The solution was stirred for 15 minutes after the addition of 0.1 ml of 85% lactic acid, poured into water, and extracted with ether. The ether layer was washed with saturated NaHCO$_3$, saturated CuSO$_4$ and then worked up in the usual way to give 98 mg (100% yield) of a colorless oil, which was immediately carried through Step 5.

| nmr (CCl$_4$) | δ 1.69 | s | 3H | —CH$_3$ |
| | 1.9-2.9 with peak at 2.12 | | | |
| | | m | 12H | methylene |
| | 5.4 | (t) | 2H | olefinic |
| | 5.9 | (s) | 1H | allylic methine |
| | 6.5-8.3 | m | 14H | aromatic |

EXAMPLE 18

3-and 1-Hydroxy-17-methyl(1,3,5(10),13(17)-gonatetraene, 7a and 7b (R = HO) by cyclization of the dibenzoate VI (R$^0$ = m—C$_6$H$_5$CO$_2$, R$^2$ = C$_6$H$_5$CO)

A sample of 0.073 mole of the crude dibenzoate VI (R$^0$ = m—C$_6$H$_5$CO$_2$,R$^2$ = C$_6$H$_5$CO) as prepared in Example 17 was cyclized by dissolving in 0.35 ml of dry methylene chloride and adding to a solution of 0.023 mmole of stannic chloride in 0.43 ml of methylene chloride under nitrogen at −75°. The yellow solution was stirred at −75° for 20 minutes, diluted with ether and pyridine, and filtered. The ether solution was washed with dilute HCl and NaHCO$_3$, followed by the usual work up. The crude benzoate mixture was dissolved in aqueous methanol, hydrolyzed with sodium hydroxide, and poured into water, and the mixture of phenols, 7a and 7b (R = HO) was extracted with ether. Glpc analysis of this mixture indicated that the molar ratio of 7a to 7b was about 1.3:1.

EXAMPLE 19

3-Methoxy-17α-methyl-13,17β-epoxy-1,3,5(10)-gonatriene, 9a (R = CH$_3$O)

A solution of 0.12 mmole of the methoxy tetracyclic olefin 7a (R = CH$_3$O) and 0.19 mmole of purified m-chloroperbenzoic acid in 0.5 ml of methylene chloride was stirred at room temperature for 1 hour. The product was isolated by diluting with ether and washing with 1N NaOH, followed by the usual work up to give 35 mg (100% yield) of solid product. Glpc analysis showed a β/α epoxide ratio of about 5.

| nmr (of crude mixture) | δ 1.0-3.0 | m | 15H | methylene & methine |
| | 1.34 | s | 3H | —CH$_3$ |
| | 1.37 | s | | —CH$_3$ |
| | 3.77 | s | 3H | CH$_3$O— |
| | 6.6-7.4 | m | 3H | aromatic |

In accordance with the subject invention, a total synthesis from simple precursors is provided for estrogenic steroids. Both natural and synthetic steroids can be synthesized by simple modifications of process steps. Good yields are achieved to the desired product, while providing for flexibility in modifying the compounds so as to be able to introduce various functionalities at different positions.

Although the foregoing invention has been described in some detail by way of illustration and example for purposes of clarity of understanding, it will be obvious that certain changes and modifications may be practiced within the scope of the appended claims.

What is claimed is:

1. Compounds of the formula

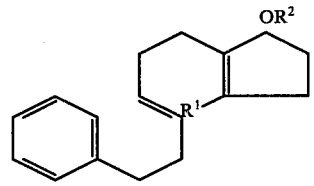

wherein the benzene ring has at least one ortho position in relation to the olefinic chain unsubstituted and free to undergo cyclization with the olefinic group to produce a six membered ring, and wherein the benzene ring may be otherwise substituted by groups that are compatible with the Wittig reaction, and R$^1$ is hydrogen or lower alkyl, and wherein R$^2$ is hydrogen, acyl moiety of a carboxylic acid having from 1 to 7 carbon atoms, tri(-lower alkyl) silyl or lower alkyl, wherein lower alkyl is of from 1 to 4 carbon atoms.

2. Compounds of claim 1, wherein the benzene ring is monosubstituted and is substituted in a position meta to the olefinic chain by OR, R being H or a removable protective group selected from the group consisting of hydrocarbyl of from 1 to 8 carbon atoms having 0 to 1 site of ethylenic unsaturation or α-alkoxyalkyl of from 2 to 6 carbon atoms.

3. Compounds according to claim 1, wherein R$^2$ is acyl moiety of a carboxylic acid.

* * * * *